United States Patent
Yokota et al.

(10) Patent No.: US 7,879,347 B2
(45) Date of Patent: Feb. 1, 2011

(54) DIHYDROXYPHENYL COMPOUNDS AND GLUCOSIDE COMPOUNDS THEREOF

(75) Inventors: Tomohiro Yokota, Odawara (JP); Shunsuke Yamazaki, Odawara (JP); Hiroko Nakatsugawa, Ayase (JP); Takeshi Ikemoto, Minamiashigara (JP); Mariko Hara, San Francisco, CA (US); Shintaro Inoue, Odawara (JP)

(73) Assignee: KAO Corporation, Tokyo (JP)

( * ) Notice: Subject to any disclaimer, the term of this patent is extended or adjusted under 35 U.S.C. 154(b) by 17 days.

(21) Appl. No.: 12/348,849

(22) Filed: Jan. 5, 2009

(65) Prior Publication Data

US 2009/0124561 A1 May 14, 2009

Related U.S. Application Data

(62) Division of application No. 11/274,565, filed on Nov. 14, 2005, now abandoned, which is a division of application No. 09/946,933, filed on Sep. 5, 2001, now Pat. No. 7,025,985.

(30) Foreign Application Priority Data

May 28, 2001 (JP) .............................. 2001-158268

(51) Int. Cl.
- A61K 8/02 (2006.01)
- A61K 31/19 (2006.01)
- A61K 31/70 (2006.01)
- A01N 37/10 (2006.01)
- A01N 43/04 (2006.01)

(52) U.S. Cl. ........................... 424/401; 514/568; 514/25
(58) Field of Classification Search .................. 424/401
See application file for complete search history.

(56) References Cited

U.S. PATENT DOCUMENTS

| | | | |
|---|---|---|---|
| 3,899,597 A | 8/1975 | Mookherjee et al. | |
| 3,920,020 A * | 11/1975 | Kraskin | 604/359 |
| 4,504,412 A | 3/1985 | Harris | |
| 4,753,958 A * | 6/1988 | Weinstein et al. | 514/410 |
| 5,554,410 A | 9/1996 | Bell et al. | |
| 5,629,338 A | 5/1997 | Okuda et al. | |
| 5,674,498 A | 10/1997 | Inoue et al. | |
| 5,908,770 A | 6/1999 | Joulain et al. | |
| 6,210,738 B1 | 4/2001 | Chen | |
| 6,482,421 B2 | 11/2002 | Weidner | |
| 6,531,118 B1 | 3/2003 | Gonzalez et al. | |
| 2002/0042441 A1 | 4/2002 | Acton et al. | |

FOREIGN PATENT DOCUMENTS

| | | |
|---|---|---|
| EP | 0 930 019 A2 | 7/1999 |
| EP | 0 930 019 A3 | 7/1999 |
| FR | 2 716 374 | 8/1995 |
| JP | 57163307 A | 10/1982 |
| JP | 61268664 A | 11/1986 |
| JP | 61268664 A * | 11/1986 |
| JP | 04202127 | 7/1992 |
| JP | 04202127 A * | 7/1992 |
| JP | 2000-169325 | 6/2000 |
| JP | 2000-239143 | 9/2000 |

OTHER PUBLICATIONS

Feingold et al. (Endocrinology, Stimulation of lipolysis in cultured fat cells by tumor necrosis factor, interleukin-1, and the interferons is blocked by inhibition of prostaglandin synthesis, vol. 130, Jan. 1992).*
Berlin et al., "Derivatives of zingerone", Zhurnal Obschei Khimii, 1949, vol. 19, pp. 569-576, Abstract, CAPLUS Abstract, CN 1949:38829.
"Phenylbutan-2-One B-D-Glucosides From Raspberry Fruit", Phytochemistry, 29, No. 12, 3853-3858 (1990).
S. Sporstol and R.R. Scheline, "The Metabolism of 4-(4-hydroxyphenyl)butan-2-one(raspberry ketone) in rats, guinea-pigs and rabbits" Xenobiotica, 1982, vol. 12, No. 4, 249-257 (1981).

* cited by examiner

Primary Examiner—Sreeni Padmanabhan
Assistant Examiner—Layla Soroush
(74) Attorney, Agent, or Firm—Birch, Stewart, Kolasch & Birch, LLP (57) ABSTRACT

A skin cosmetic composition comprising the compound represented by the following formula (1):

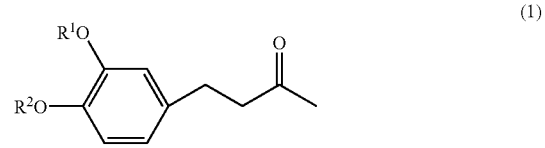

(1)

wherein $R^1$ is hydrogen and $R^2$ is hydrogen or glucose residue.

8 Claims, 5 Drawing Sheets

DIHYDROXYPHENYL COMPOUNDS AND GLUCOSIDE COMPOUNDS THEREOF

This application is a Divisional of application Ser. No. 11/274,565 filed on Nov. 14, 2005 now abandoned, which is a Divisional of application Ser. No. 09/946,933 filed on Sep. 5, 2001 (now U.S. Pat. No. 7,025,985, issued Apr. 11, 2006) and for which priority is claimed under 35 U.S.C. §120. This application also claims priority of Application No. 2001-158268 filed in Japan on May 28, 2001 under 35 U.S.C. §119. The entire contents of each of the above-identified applications are hereby incorporated by reference.

FIELD OF THE INVENTION

The present invention relates to dihydroxyphenyl compounds and glucoside compounds thereof which are useful to reform obese constitution by promoting shrinkage of general or topical fatty tissues, or to suppress or prevent obesity by preventing the fatty tissue from swelling.

The present invention relates also to dihydroxyphenyl compounds and glucoside compounds thereof which are effective for skin whitening.

DESCRIPTION OF THE PRIOR ART

Intercorporal fat is neutral fat present in white adipose tissues produced from surplus energy intake remaining after energy consumption. Obesity due to heavily accumulated intercorporal fat is not only aesthetically unfavorable, but also causes various diseases, such as arteriosclerosis. Recently, more and more people suffer from obesity due to excessive eating, lack of exercise, and/or stress. On the other hand, a slim and tight body is yearned for particularly by women from the viewpoint of appearance. Accumulation of subcutaneous fat is unfavorable for health, so that reduction of the fat or prevention of the accumulation thereof is important.

Meanwhile, capsaicin contained in Capsicum is known to be capable of preventing obesity by bonding to blood albumin and secreting hormone which promotes adrenal metabolism and activates energy metabolism in lever or fat cells (Kazuo Iwai and Nobuji Nakatani, Function of Spice Ingredients in Foods, 97 (1989), Koseikan, Tokyo). However, capsaicin is strongly irritant and thus has limited applications or is used in a limited amount.

The present inventors speculated that it is difficult to diminish accumulated fat cells, but it is easier to make the cells smaller by decomposing lipid droplets in the cells.

The lipid droplet can be decomposed with an enzyme, phospholipase C, in a similar manner as protein. However, it is surrounded by a hydrophobic phospholipid membrane, so that the enzyme present in endoplasmic reticulum which is a mass of water cannot obtain access to the lipid droplet.

Meanwhile, sympathetic nerves are activated by taking exercise to secrete fat decomposing hormone: This hormone is believed to remove the phospholipid membrane to allow the enzyme to obtain access the lipid droplets to thereby promote lypolysis. Therefore, the present inventors endeavored to find a substance which promotes accessibility of the enzyme to the lipid droplets in a similar manner as the hormone.

As a result, the present inventors found that raspberry ketone, gingerone and derivatives thereof promote decomposition of fat accumulated in fatty tissues and, thus, are effective to suppress obesity or to reform obese constitution (Japanese Patent Application Laid-open No. 2000-169325). However, both raspberry ketone and gingerone have their peculiar odor and taste and consequently their amounts of dosage and versatility are limited.

Thus, a lypolysis promoter, skin cosmetic composition, and food or drink composition which have satisfactory versatility and an effect of preventing formation of or reducing subcutaneous fat are desired.

Meanwhile, there is strong desire for white skin and, accordingly, it is desired to prevent or lighten erythema, melanization, stains, or freckles due to skin damages caused by UV light. To lighten the damage caused by UV light leads to suppressing photo-aging which causes wrinkles. Thus, a skin cosmetic composition having effects of preventing erythema and of whitening is desired.

In view of the above discussion, it is an object of the present invention to provide a substance which is effective for reforming obese constitution by promoting shrinkage of general or topical fat tissues, or suppressing or preventing obesity by preventing swelling of the fat tissues, and which substance has no odor or taste and has excellent versatility.

Another object of the present invention is to provide a skin cosmetic composition which has an excellent whitening effect.

SUMMARY OF THE INVENTION

The present inventors have found that a compound represented by the following formula (1):

(1)

where one of $R^1$ and $R^2$ is hydrogen and the other one is hydrogen or glucose residue, is effective for reforming obese constitution or suppressing or preventing obesity by promoting lypolysis and has whitening effect to thereby attain the aforesaid objects.

Thus, the present invention is a skin cosmetic composition comprising the compound represented by the above formula (1).

Preferably, the compound is incorporated in an amount, based on the weight of the composition, of from 0.001 to 20 wt %, more preferably of from 0.01 to 5 wt %, and most preferably of from 0.05 to 3 wt %.

Another aspect of the present invention is a method for reducing a body weight or inhibiting melanogenesis by applying the aforesaid cosmetic composition.

DESCRIPTION OF THE PREFERRED EMBODIMENTS

The present invention will be explained in detail.

Japanese Patent Application No. 11-42937 by the present applicant was published on Sep. 5, 2000, which describes some species of the present compound as an active ingredient for a skin cosmetic composition having melanogenesis inhibition effect.

The compound of the aforesaid formula (1) wherein $R^1$ and $R^2$ are both hydrogen, 4-(3',4'-dihydroxyphenyl)-butane-2-one, may be easily prepared by the method described in the above application. Specifically, it may be easily prepared by cleavage of C—O bond of methylether of gingerone, [4-(3'-methoxy-4'-hydroxyphenyl)-butane-2-one], which is contained in ginger, in a known manner with, for example, boron tribromide or hydriodic acid.

The compound of the formula (1) wherein $R^1$ or $R^2$ is glucose residue may be obtained by extracting it from plants, such as raspberries, with an appropriate solvent and, if necessary, condensing or evaporating the solvent to dryness in a known method (see Phytochemistry, Vol. 29, No. 12, 3853-3858 (1990)). Alternatively, it may be prepared by condensing 3,4-dihydroxy benzaldehyde with acetone and reducing the condensate by a conventional method.

The compound of the aforesaid formula (2) wherein $R^1$ and $R^2$ are both hydrogen, 4-(3',4'-dihydroxyphenyl)-butane-2-ol, may be prepared in a similar manner as described above, starting from 4-(3'-methoxy-4'-hydroxyphenyl)-butane-2-ol obtained by reducing gingerone with sodium borohydride. It may also be prepared by reducing the compound of the formula (1) by a conventional method.

The compound of the formula (1) or (2) may be used alone or in combination of two or more of them as a lypolysis promoter or a whitening agent. An amount of the present compound to be incorporated in a skin cosmetic composition or a food or drink composition intended to be used for reducing weight may vary depending on the form of the composition. In the skin cosmetic composition for reducing weight, the present compound is incorporated preferably in an amount of from 0.001 to 20 wt %, more preferably from 0.01 to 5.0 wt %, most preferably from 0.05 to 3.0 wt % based on the weight of the composition. In the food or drink composition for reducing weight, the present compound is incorporated preferably in an amount of from 0.001 to 20 wt %, more preferably from 0.01 to 10.0 wt %, most preferably from 0.01 to 3.0 wt % based on the weight of the composition. If the amount is less than the aforesaid lower limit, an effect of the present invention may not be attained. If the amount is more than the aforesaid upper limit, the effect may not increase correspondingly. In a skin cosmetic composition with a major purpose of whitening, the present compound is incorporated preferably in an amount of from 0.01 to 5 wt % based on the weight of the composition.

In the present skin cosmetic composition, any known substances can be incorporated in addition to the aforesaid present compound, for example, those conventionally used in a skin cosmetic composition such as fats and oils, pigments, surfactants, humectants, UV absorbers, anti-inflammatories, fungicides, antiseptics, and colorants; β-adrenaline action stimulants, such as Butopamine and isoproterenol; α2-adrenaline action depressants such as yohimbin and ergotoxine; xanthin derivatives, such as theophylline and caffeine; bipyridine derivatives, such as Milrinone and Amrinone; and those which suppress or prevent obesity, such as raspberry ketone and gingerone.

In the present food or drink composition, any known substances can be incorporated in addition to the aforesaid present compound, for example, those conventionally used in a food or drink composition, such as saccharides, perfumes, emulsifiers, milk products, proteins, stabilizers, colorants, acidulants, fats and oils, cereals, eggs, gum base; xanthin derivative such as caffeine; hydroxy citric acid; and those which suppress or prevent obesity, such as capsaicin, raspberry ketone, gingerone and synephrine.

The present lypolysis promoter can be incorporated in food, oral drugs, or skin cosmetics in any dosage form. For example, the lypolytic skin cosmetics may be of a form of cream, milky lotion, gel, stick, sheet, cataplasm, powder, liquid or granule to be applied to skin, for bathing, or for washing. The food or drink composition may be incorporated in chewing gum, chocolate, candies, gummy jellies, soup, ice cream, noodles, or bakery products.

EXAMPLES

The present invention will be explained in details with reference to the following Examples and Comparative Examples. Efficacy of lypolysis promotion was evaluated in the lypolysis test and in the subcutaneous fat decomposition test described below. Commercially available raspberry ketone and gingerone were used.

Preparation Example 1

4-(3',4'-dihydroxyphenyl)-butane-2-one

Figure 1:
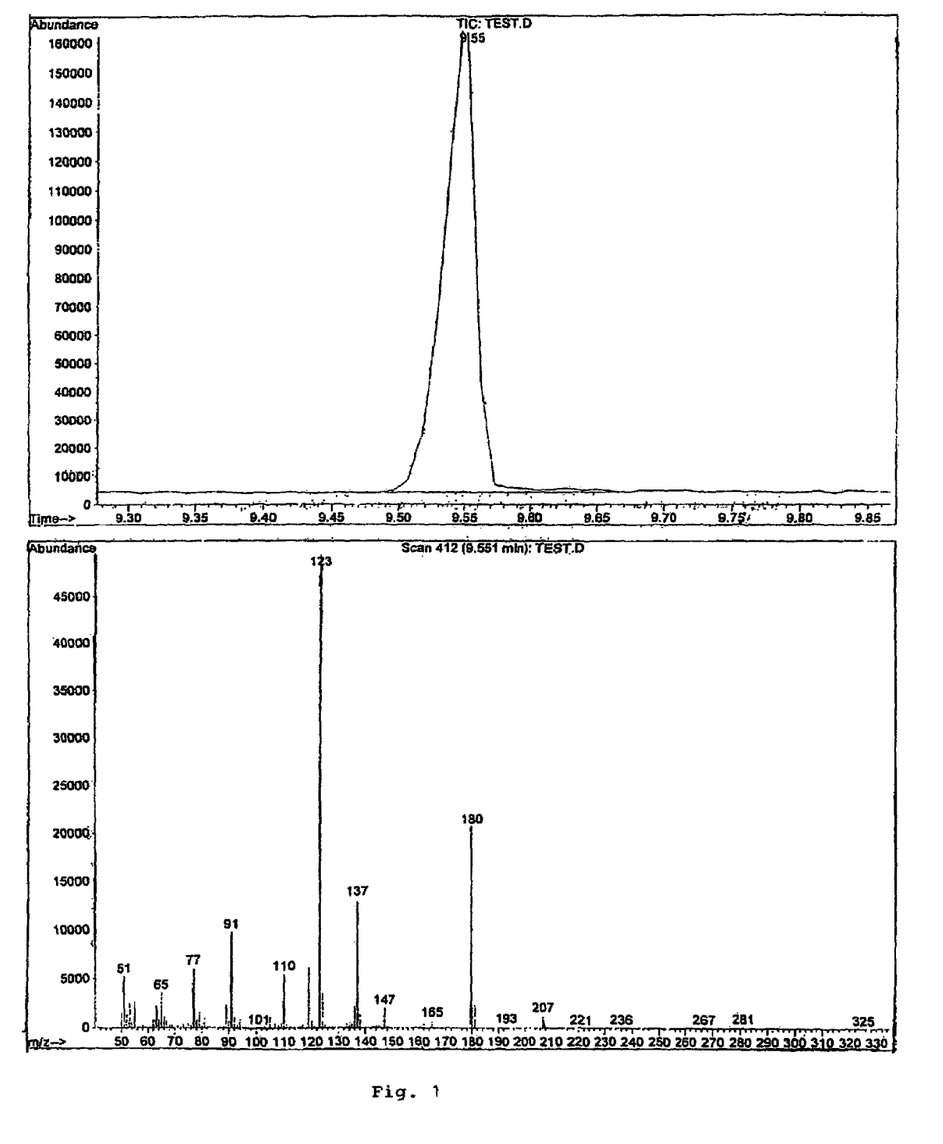
FIG. 1 shows a GC-MS total ion chromatogram (top) and a mass spectrum (bottom) of 4-(3',4'-dihydroxyphenyl)-butane-2-one of the present invention.
Figure 2:
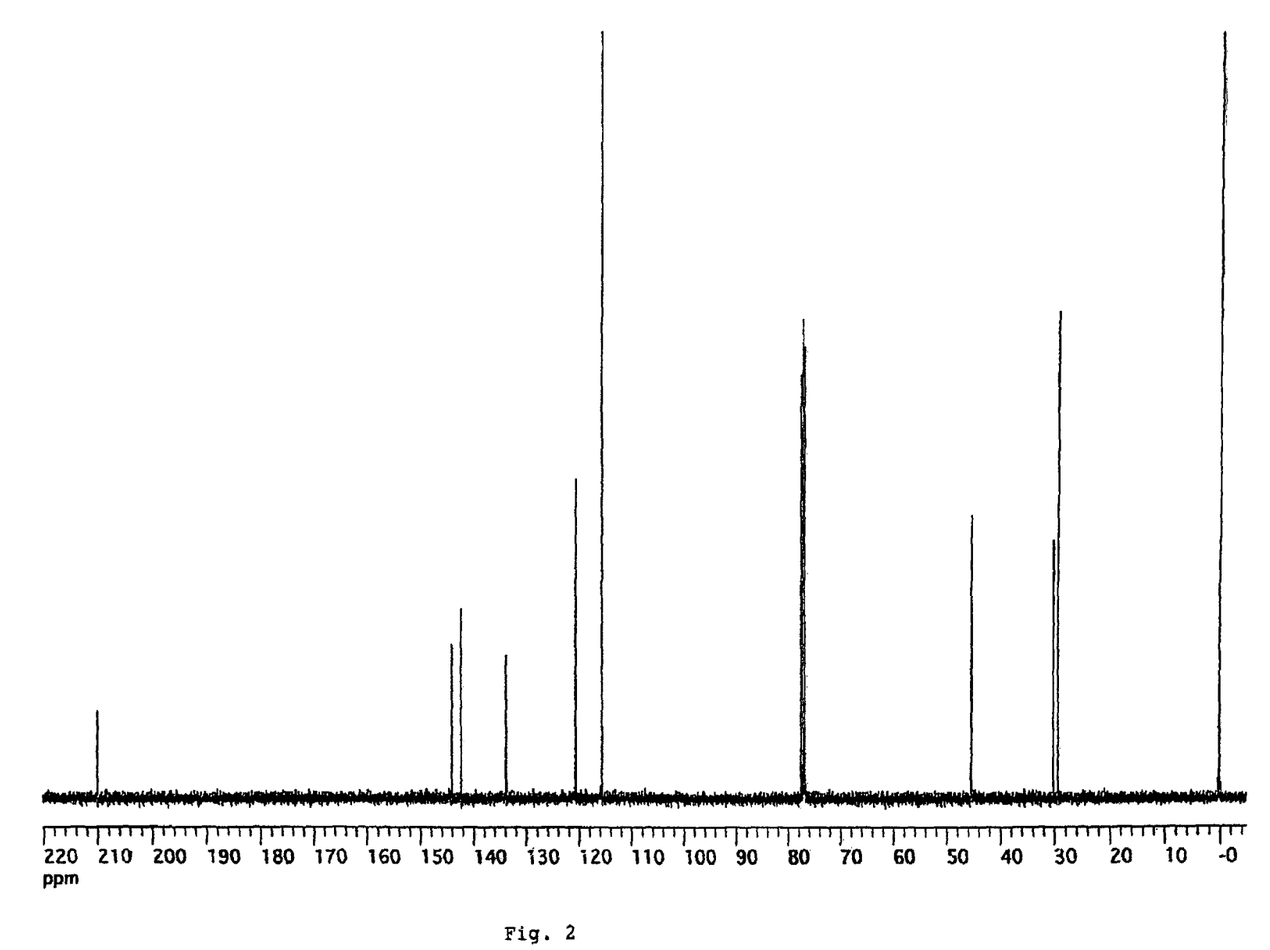
FIG. 2 shows a $^{13}$C-NMR spectrum of 4-(3',4'-dihydroxyphenyl)-butane-2-one of the present invention.

Gingerone, 4-(3'-methoxy-4'-hydroxyphenyl)-butane-2-one), was dissolved in dichloromethane, to which 1.0 mol/l boron tribromide solution in dichloromethane was then added at −30° C. While stirring, the reaction mixture was gradually heated to a room temperature and allowed to react for further 2 hours at the temperature. After adding ice water to the reaction mixture, an aqueous 2% sodium hydrogen carbonate solution was added. Then, the reaction mixture was extracted with ethyl acetate, and the ethyl acetate layer thus obtained was dried with anhydrous magnesium sulfate. Then, the ethyl acetate layer was vacuum condensed to obtain brown oil which was purified by silica gel chromatography, using a mixture of hexane/ethyl acetate=7/3 as a developing solvent. The white crystals thus obtained had almost no taste and no odor. Chemical structure was confirmed to be 4-(3',4'-dihydroxyphenyl)-butane-2-one by GC-MS and NMR (see FIGS. 1 and 2).

Preparation Example 2

4-(3',4'-dihydroxyphenyl)-butane-2-ol

Figure 3:
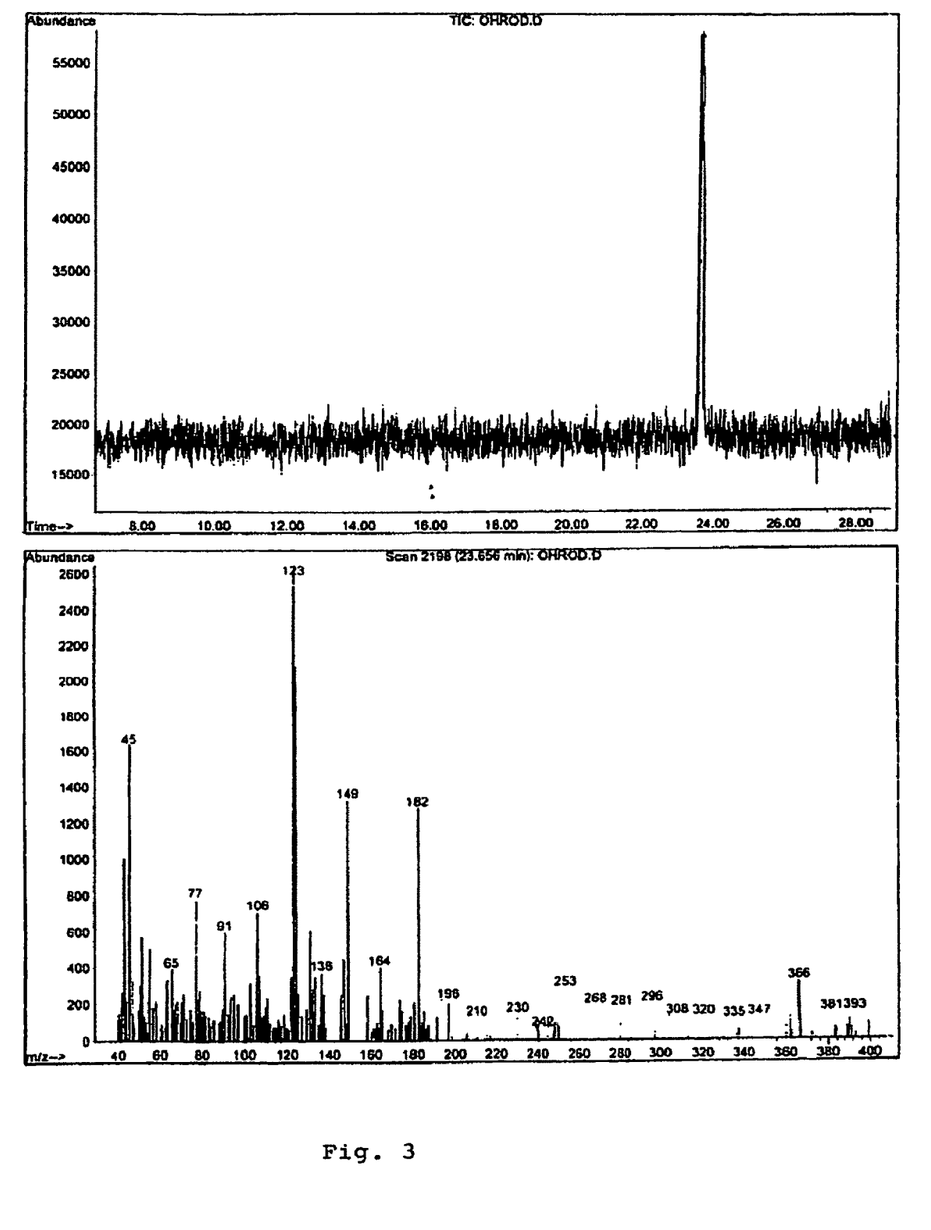
FIG. 3 shows a GC-MS total ion chromatogram and a mass spectrum of 4-(3',4'-dihydroxyphenyl)-butane-2-ol of the present invention.
Figure 4:
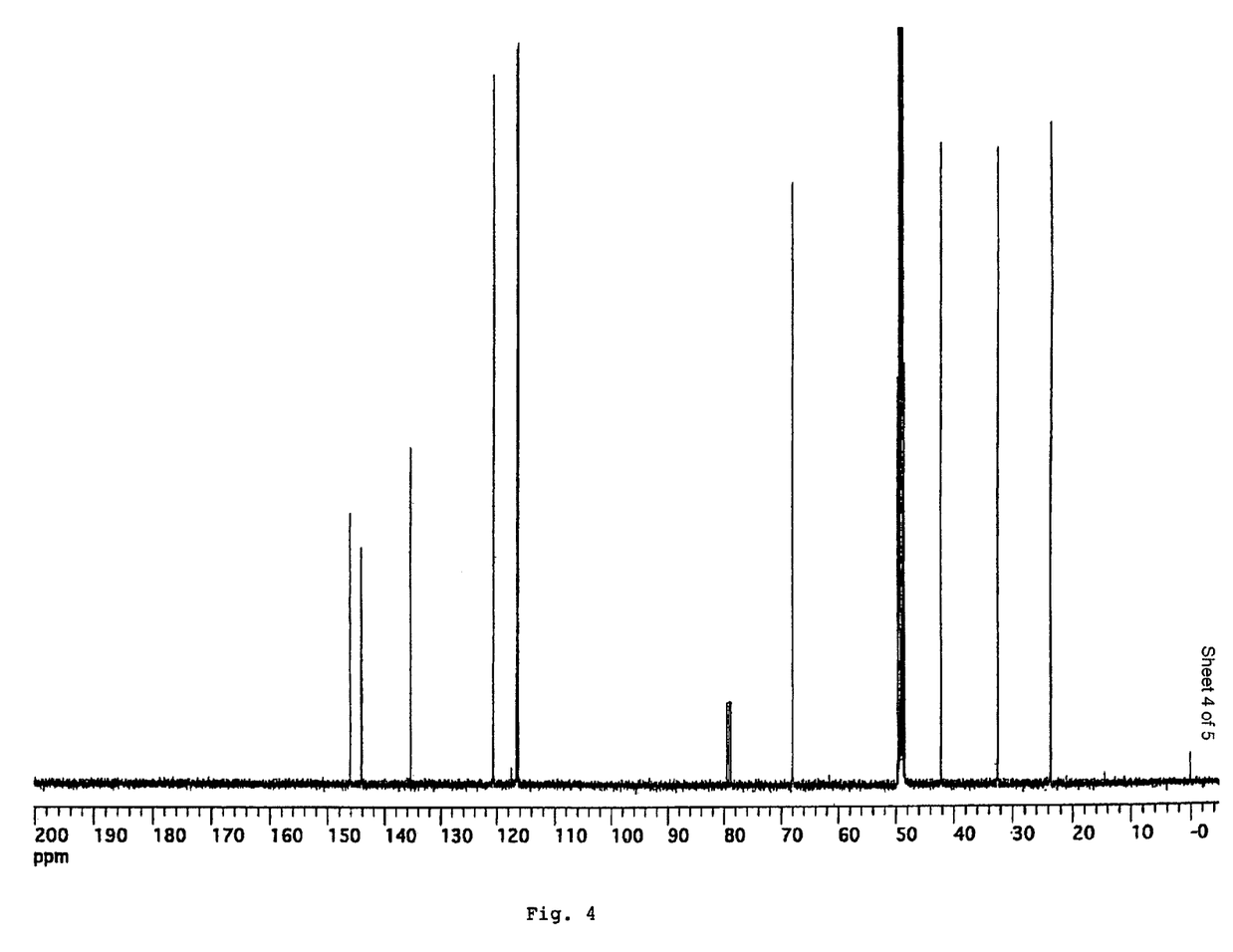
FIG. 4 shows a $^{13}$C—NMR spectrum of 4-(3',4'-dihydroxyphenyl)-butane-2-ol of the present invention.
Figure 5:
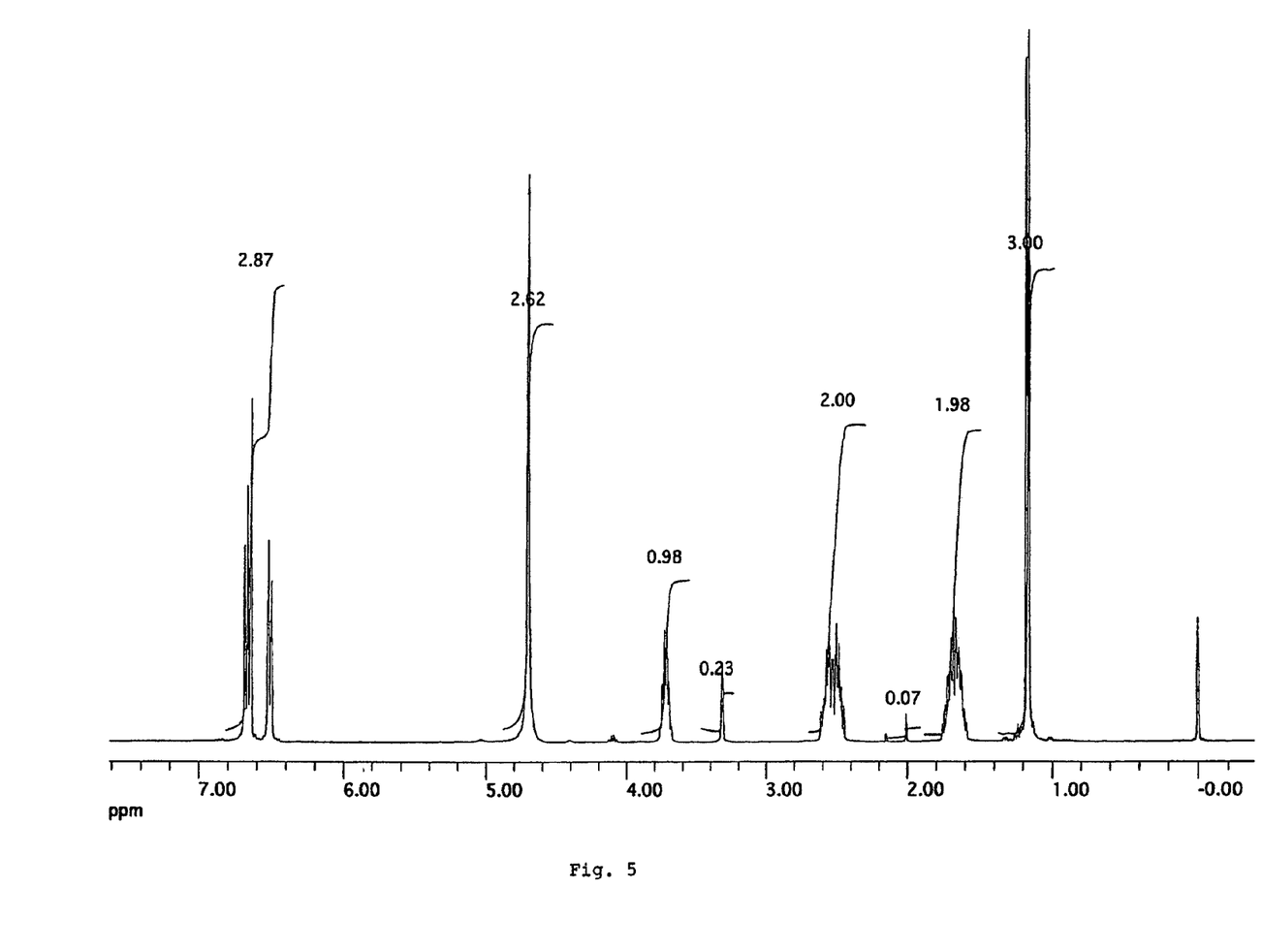
FIG. 5 shows a $^1$H—NMR spectrum of 4-(3',4'-dihydroxyphenyl)-butane-2-ol of the present invention.

The procedures in preparation Example 1 were repeated except that use was made of 4-(3'-methoxy-4'-hydroxyphenyl)-butane-2-ol obtained by reducing gingerone with sodium borohydride, instead of gingerone. The white crystals thus obtained had almost no taste and no odor. Chemical structure was confirmed to be 4-(3',4'-dihydroxyphenyl)-butane-2-ol by GC-MS and NMR (see FIGS. 3, 4 and 5).

Method for Determination of Lypolytic Activity

Free fatty cells were prepared from epididymis fatty tissues of Wister male rats (body weight, 150 to 200 g) using a collagenase solution, according to Rodbell's method (M.

Rodbell, J. Bioo. Chem., 239, 375 (1964)). The cells were added to a Hank's balanced solution containing 0.05 μg/ml of bovine serum albumin, 0.05 μg/ml of norepinephrine and 100 μg/ml of the present compound to be tested, and then allowed to react at 37° C. for 1 hour. Liberated fatty acids were extracted and quantitated with a copper reagent and a color developing reagent. Lypolytic activity was calculated according to the following equation.

Lypolytic activity(%)=[$A/B$]×100, wherein A: amount of fatty acids in a sample solution, and B: that in a control solution without present compound.

Subcutaneous Fat Decomposition Test

Wister rats (male, 7 to 9 weeks old) were shaved at their bellies. Then, the belly cortex was enucleated together with subcutaneous fatty tissues and mounted on Franz-type diffusion cells with a diameter of 2 cm. The keratin held in the upper cell was uniformly coated with 0.5 g of the present skin cosmetic composition and the lower cell for the subcutaneous tissue side was filled with a physiological saline solution buffered at pH 7.2 with a phosphate buffer solution. After keeping the cell at 37° C. for 6 hours, an aliquot of the buffer solution was taken out from the lower cell and glycerol liberated in the solution was quantitated by an enzyme method with F-kit Glycerol, ex Beringer Manheim Co. For each sample, the quantification was repeated five times and data were averaged.

Example 1 and Comparative Example 1

The lypolytic activity was determined on the present lypolysis promoter and raspberry ketone for comparison.

TABLE 1

|  | Lypolysis promoter | degree of lypolysis promotion (%) |
|---|---|---|
| Example 1 | 4-(3',4'-dihydroxyphenyl)-butane-2-one | 194.3 +/− 12.4 $p < 0.001$ |
| Comparative Example 1 | Raspberry ketone | 142.0 +/− 6.8 $p < 0.01$ |

The present lypolysis promoter of Example 1 showed significantly higher lypolytic activity, compared with raspberry of Comparative Example 1.

Examples 2, 3 and Comparative Examples 2 and 3

Gel Type Skin Cosmetic Composition for Reducing Weight

Parts A and B were separately prepared by mixing and dissolving the substances in the amounts as shown in Table 2 in a conventional method. Then Part B was added to Part A with stirring to obtain a gel type skin cosmetic composition for reducing weight.

TABLE 2

| Part (wt %) | Example 1 | Example 2 | Comparative Example | Referential Example |
|---|---|---|---|---|
| Part A |  |  |  |  |
| 4-(3',4'-dihydroxyphenyl)-butane-2-one | 1.0 | 3.0 | — | — |
| Raspberry ketone | — | — | — | 1.0 |
| Glycerol | 10.0 | 10.0 | 10.0 | 10.0 |
| Carboxyvinyl polymer | 0.3 | 0.3 | 0.3 | 0.3 |
| Disodium edetate | 0.1 | 0.1 | 0.1 | 0.1 |
| Purified water | balance | balance | balance | balance |
| Diisopropanolamine | 1.0 | 1.0 | 1.0 | 1.0 |
| Squalane | 10.0 | 10.0 | 10.0 | 10.0 |
| Part B |  |  |  |  |
| Polyoxyethylene(60) hydrogenated castor oil | 0.8 | 0.8 | 0.8 | 0.8 |
| Carrageenan | 3.0 | 3.0 | 3.0 | 3.0 |
| Xanthan gum | 3.0 | 3.0 | 3.0 | 3.0 |
| Polyvinylalcohol | 2.0 | 2.0 | 2.0 | 2.0 |
| Ethanol | 45.0 | 45.0 | 45.0 | 45.0 |
| Menthol | 0.1 | 0.1 | 0.1 | 0.1 |
| Perfume | q.s. | q.s. | q.s. | q.s. |

The results of the subcutaneous fat decomposition test on the aforesaid gel type skin cosmetic compositions are as shown in Table 3.

TABLE 3

|  | Liberated Glycerol (μmol/ml) |
|---|---|
| Example 2 | 174.5 |
| Example 3 | 191.6 |
| Comparative Example 2 | 132.4 |
| Comparative Example 3 | 60.8 |

Example 4 and Comparative Examples 4 and 5

In Vivo Test on Obesity by High Calorie Diet

Each seven ICR mice per group (female, 5-week old at the beginning of the test, average body weight of 31 g) were bred for 3 weeks with high-calorie diet (Comparative Example 4) or high-calorie diet to which 4-(3',4'-dihydroxyphenyl)-butane-2-one was added (Example 4) or a standard feed (solid standard feed MF, ex Oriental Yeast Co.) for a control group (Comparative Example 5). The mice were allowed to freely intake feed and drinking water, and weighed on the final day of the test period. Composition of the feed and the results are as shown in Tables 4 and 5, respectively.

TABLE 4

| Feed Composition | | | |
|---|---|---|---|
| Comparative Example 5 (Control) |  | Example 4 wt % | Comparative Example 4 wt % |
| Solid standard feed MF, ex Oriental Yeast Co. | Beef tallow | 40 | 40 |
|  | Corn starch | 10 | 10 |
|  | Granulated sugar | 9 | 9 |
|  | Mineral[1] | 4 | 4 |
|  | Vitamine[2] | 1 | 1 |
|  | Casein | 35 | 36 |
|  | 4-(3',4'-dihydroxyphenyl)-butane-2-one | 1 | — |

[1] AIN mineral mix, ex ICN Co.
[2] AIN vitamin mix,

TABLE 5

| | Results | | |
|---|---|---|---|
| | Comparative Example 5 (Control) | Example 4 | Comparative Example 4 |
| Average weight (g) | 38.1 | 38.4 | 43.2 |
| Weight increment (g) | 7.1 | 7.4 | 12.2 |

Example 5

Melanogenesis Inhibition Test

B16 melanoma cells were inoculated in a 12 wells-plastic plate at a concentration of $2\times10^4$/well on MEM (Minimum Essential Medium). After 24 hours, the medium was changed to a Theophylline containing medium to which 4-(3',4'-dihydroxyphenyl)-butane-2-one was added in the concentrations shown in Table 6. The cells were cultured for 72 hours and then treated with 10% TCA and ethanol/diethylether(=1/1). After counting the number of the cells, the cells were dissolved in an aqueous 1 mol/l sodium hydroxide solution containing dimethylsulfoxide in a concentration of 10%. Optical density at 475 nm (OD475) of the solution thus obtained was measured. The amount of the produced melanin per cell was calculated from OD475 and expressed in percentage relative to the amount observed in the blank sample where cells were cultured on a medium which did not contain 4-(3',4'-dihydroxyphenyl)-butane-2-one.

TABLE 6

| 4-(3',4'-dihydroxyphenyl)-butane-2-one concentration (μg/l) | Amount of melanin per cell (%) | Standard deviation |
|---|---|---|
| 0 | 100 | 11.2 |
| 1 | 94.7 | 3.4 |
| 3 | 77.2 | 2.2 |
| 10 | 62.7 | 2.5 |
| 30 | 2.2 | 0.3 |

There was no difference among the numbers of the cells in the aforesaid concentration range of the present compound.

Example 6

Anti-Oxidation Test

To 1 ml of methyl linolate, 0.005 g of the present compound was added, which was then irradiated with UV light with a UV light irradiation apparatus, M-DMR, ex Toshiba Co. The amount of peroxides formed by oxidation of methyl linolate was determined according to a method described in Akasaka et al., Bioscience/Biotechnology/Biochemistry, Vol. 58, 396 (1994), using diphenyl-1-pyrenylphosphine as a fluorescent labeling agent. Comparative test on raspberry ketone was made in the same manner as above. The results are as shown in Table 7.

TABLE 7

| | UVB 10 (J/cm$^2$) | UVB 30 (J/cm$^2$) |
|---|---|---|
| Raspberry ketone | 30.2 | 42.5 |
| 4-(3',4'-dihydroxyphenyl)-butane-2-one | 1.6 | 3.7 |

Examples 7 to 12

Skin lotion were prepared from the components as shown below and in Table 8.

| Parts | Amount (wt %) |
|---|---|
| (A) | |
| Ethanol | 10.0 |
| Monolauric acid polyoxyethylene(20) sorbitan | 5.0 |
| Dibutylhydroxytoluene | 0.01 |
| Perfume | 0.05 |
| (B) | |
| The present compound described in Table 8 | |
| (C) | |
| Glycerol | 5.0 |
| Xanthan gum | 0.1 |
| Hydroxyethylcellulose | 0.1 |
| Purified water | balance |

TABLE 8

| | Sample | Amount (wt %) |
|---|---|---|
| Example 7 | 4-(3',4'-dihydroxyphenyl)-butane-2-one | 3.0 |
| Example 8 | 4-(3',4'-dihydroxyphenyl)-butane-2-one | 0.5 |
| Example 8 | 4-(3',4'-dihydroxyphenyl)-butane-2-one | 0.01 |
| Example 10 | 4-(3',4'-dihydroxyphenyl)-butane-2-ol | 3.0 |
| Example 11 | 4-(3',4'-dihydroxyphenyl)-butane-2-ol | 0.5 |
| Example 12 | 4-(3',4'-dihydroxyphenyl)-butane-2-ol | 0.01 |

Preparation Method

Part B was homogeneously dissolved in Part C, to which Part A was added with stirring to be dispersed homogeneously. The product thus obtained was poured in a container.

Examples 13 to 18, and Comparative Examples 5 and 6

Skin Cream

Skin creams were prepared from the components shown below and in Table 9.

| Part | Amount (wt %) |
|---|---|
| (A) | |
| Glycerol monostearate | 2.0 |
| Bees wax | 1.0 |

-continued

| Part | Amount (wt %) |
|---|---|
| Monooleic acid polyoxyethylene(6) Sorbitan | 1.0 |
| Vaseline | 4.0 |
| Liquid paraffin | 12.0 |
| (B) | |
| The present compound described in Table 9 | |
| (C) | |
| Sodium N-stearoyl-L-glutamate | 5.0 |
| Carrageenan | 0.3 |
| Mthylparaben | 0.1 |
| Purified water | balance |

TABLE 9

| | Sample | Amount (wt %) |
|---|---|---|
| Example 13 | 4-(3',4'-dihydroxyphenyl)-butane-2-one | 3.0 |
| Example 14 | 4-(3',4'-dihydroxyphenyl)-butane-2-one | 0.5 |
| Example 15 | 4-(3',4'-dihydroxyphenyl)-butane-2-one | 0.01 |
| Example 16 | 4-(3',4'-dihydroxyphenyl)-butane-2-ol | 3.0 |
| Example 17 | 4-(3',4'-dihydroxyphenyl)-butane-2-ol | 0.5 |
| Example 18 | 4-(3',4'-dihydroxyphenyl)-butane-2-ol | 0.01 |

Preparation Method

Part A and a mixture of Components B and C were separately heated to 80° C. to make homogeneous solutions. Then, Part A was added to the mixture of Parts B and C and emulsified. The emulsion thus obtained was cooled to 30° C. with stirring.

Example 19

Chewing Gum

Chewing gum with the following composition was prepared.

| | wt % |
|---|---|
| Gum base | 20 |
| Maltitol | 73.5 |
| Reduced thick malt syrup | 4 |
| Apple flavor | 0.5 |
| *Carcinia Cambogia* Extract*[1] | 1 |
| 4-(3',4'-dihydroxyphenyl)-butane-2-one | 1 |

*[1]*Carcinia Cambogia* Extract, Citrimax HCA-500-F (trade name), ex Interhealth Co., containing 47.5% of hydroxycitric acid (HCA).

Example 20

Sweet Tablets

Sweet tablets with the following composition was prepared.

| | wt % |
|---|---|
| Sorbitol | 72.9 |
| Sucrose ester of fatty acid | 4 |
| Raspberry flavor | 0.1 |
| *Carcinia Cambogia* Extract | 3 |
| 4-(3',4'-dihydroxyphenyl)-butane-2-one | 10 |

What is claimed is:

1. A method for inducing lipolytic activity, comprising the step of applying to the skin a composition comprising a compound represented by the following formula (1), (1)

wherein one of $R^1$ and $R^2$ is hydrogen and the other one is hydrogen or glucose residue, and a topical carrier suitable for application to the skin.

2. The method according to claim 1, wherein the compound is incorporated in an amount of from 0.001 to 20 wt % based on the weight of the composition.

3. The method according to claim 1, wherein the compound is incorporated in an amount of from 0.01 to 5 wt % based on the weight of the composition.

4. The method according to claim 1, wherein the compound is incorporated in an amount of from 0.05 to 3 wt % based on the weight of the composition.

5. The method according to claim 1, wherein $R^1$ and $R^2$ are both hydrogen.

6. The method according to claim 5, wherein the compound is incorporated in an amount of from 0.001 to 20 wt % based on the weight of the composition.

7. The method according to claim 5, wherein the compound is incorporated in an amount of from 0.01 to 5 wt % based on the weight of the composition.

8. The method according to claim 5, wherein the compound is incorporated in an amount of from 0.05 to 3 wt % based on the weight of the composition.

* * * * *